US006926814B2

(12) United States Patent
Koenemann et al.

(10) Patent No.: US 6,926,814 B2
(45) Date of Patent: Aug. 9, 2005

(54) AUTOMATABLE MEASURING, CLEANING AND CALIBRATION DEVICE FOR PH-ELECTRODES OR ELECTRODES FOR MEASURING REDOX POTENTIALS

(75) Inventors: Ralf Koenemann, Stuttgart (DE); Bernhard Beck, Stuttgart (DE); Detlev Wittmer, Maulbronn (DE)

(73) Assignee: Endress & Hauser Conducta Gesellschaft fur Mess-und RegeltechnikmbH & Co., Gerlingen (DE)

( * ) Notice: Subject to any disclaimer, the term of this patent is extended or adjusted under 35 U.S.C. 154(b) by 151 days.

(21) Appl. No.: 10/116,198

(22) Filed: Apr. 3, 2002

(65) Prior Publication Data

US 2004/0069619 A1 Apr. 15, 2004

(30) Foreign Application Priority Data

Apr. 3, 2001 (DE) .......................................... 101 16 614

(51) Int. Cl.[7] .......................... G01N 27/26; F04B 41/00; B67D 5/60
(52) U.S. Cl. ........................ 204/409; 204/433; 204/402; 204/416; 417/36; 417/236; 417/237; 222/145.1; 422/82.03
(58) Field of Search .......................... 204/225, 400–402, 204/406–409, 416, 433; 222/145.1; 417/17, 26, 36, 201, 202, 352, 355, 237, 236; 422/82.03

(56) References Cited

U.S. PATENT DOCUMENTS 3,556,950 A * 1/1971 Dahms ....................... 205/775

| 4,852,385 | A | | 8/1989 | Brinkmann ................... 73/1 R |
| 5,011,587 | A | | 4/1991 | Schmidt ...................... 204/401 |
| 5,511,408 | A | * | 4/1996 | Yoshioka et al. ............ 73/1.03 |
| 5,771,933 | A | * | 6/1998 | Akamatsu et al. ....... 137/627.5 |
| 6,224,347 | B1 | * | 5/2001 | Clark et al. .............. 417/222.1 |

OTHER PUBLICATIONS

Step Motors Reference Guide, Aug. 7, 2000, Advanced Micro System, Inc., pp. 1–4.* http://web.archive.org/web/20000610203026/http://machinedesign.com, Jun. 6, 2000.*

* cited by examiner

*Primary Examiner*—Nam Nguyen
*Assistant Examiner*—R Michelle Vestal
(74) *Attorney, Agent, or Firm*—Young & Basile, P.C.

(57) ABSTRACT

An automatable measuring, cleaning and calibrating device for pH-electrodes or electrodes for measuring redox potentials, specifically in process engineering, having an electrode armature which keeps the measuring electrode in an operating position or in a maintenance position, whereby the electrode is retained in the maintenance position in a rinsing chamber in which a cleaning and calibration procedure can be performed. The device has a pump device to supply cleaning fluid and calibration solutions to the rinsing chamber over a delivery line connecting the pump device and the rinsing chamber. In order to configure the device more compactly, the pump device includes several feeds on its intake side, and a device is furnished to selectively activate a particular feed, and the media (cleaning fluid, calibration solution, etc.) brought selectively over the particular feeds to the pump device reach the rinsing chamber over the common delivery line.

19 Claims, 4 Drawing Sheets

AUTOMATABLE MEASURING, CLEANING AND CALIBRATION DEVICE FOR PH-ELECTRODES OR ELECTRODES FOR MEASURING REDOX POTENTIALS

BACKGROUND

The invention relates to an automatable measuring, cleaning and calibration device for pH-electrodes or electrodes for measuring redox potentials, specifically in process engineering, having an electrode armature which maintains the measuring electrode in an operating position or in a position for maintenance, where the electrode is retained in the maintenance position in a rinsing chamber in which a cleaning and calibration procedure can be carried out, and having a pump device to supply cleaning fluid and calibration solutions to the rinsing chamber by way of a delivery line connecting the pump device and the rinsing chamber.

Electrochemical sensors and their electrodes are only conditionally consistent with respect to their measurement characteristics as a result of the effects of temperature, type and concentration of ions in the test medium, contamination and ageing, and for this reason they should be cleaned at appropriate intervals and checked through the use of standardized calibration solutions. In an inspection of this kind sensor, parameters such as zero point and steepness of the sensor curve are captured through measurements and saved in the appropriate measurement and evaluation device for consideration during sensor operation.

An electrode armature for a measuring, cleaning and calibration device is described, for example, in DE 39 27 282 A Using an electrode armature of this type, a pH-electrode, for example, can be moved from its operating position in a process container and brought into a position for maintenance in a rinsing chamber, where it is exposed to cleaning and calibration solutions.

Further efforts are being made to automate this cleaning and calibration process, which is hereafter described as maintenance. The known method is to supply cleaning fluids and calibration solutions through pump equipment to the rinsing chamber of the measuring, cleaning and calibrating device. A separate pump device is used for each medium to be supplied.

The object of the present invention is to design a more compact version of an automatable measuring, cleaning and calibration device of the type described above.

SUMMARY OF THE INVENTION

This object is achieved under the invention in the case of a device by which the pump device comprises several feeds on its intake side, by which a device for selectively activating a particular feed, and by which the media selectively brought over the particular feeds to the pump device, i.e. cleaning fluid, calibration solutions or rinse water, reach the rinsing chamber through the common delivery line.

It is therefore proposed with the present invention that specifically only a single pump device be used, which is then connected to several feeds, for example, to several feed lines, which for their part are connected to various receiving containers for different calibration solutions and for different cleaning or rinsing solutions furnished directly at the device or at a remote location. By means of the device for selectively activating a particular feed, the feed desired at the time in accordance with the preselected cleaning and calibration cycle can be activated so that the appropriate cleaning fluid can be delivered through the pump device to the rinsing chamber.

The cleaning and calibration sequence is designed such that cleaning fluids and calibration solutions, but also rinsing solutions and compressed air if needed, can be delivered alternately to the rinsing chamber in order to service the sensor, its pH-electrode or its redox electrode, respectively.

A typical cleaning and calibration cycle for a pH-measuring electrode could run as follows: First, the measuring electrode, which has been moved from the operating to the maintenance position, is pre-rinsed with water. This is followed by a cleaning step by rinsing the chamber with cleaning fluid. Immediately afterwards water is used to provide a second rinse. The rinsing chamber is then blown dry with compressed air. A first calibration solution is introduced in the form of a pH-buffered primary solution, and the corresponding values for the sensor are determined, processed metrologically and saved. Another rinse with water is performed, followed by further blowing dry with air. Then a second calibration solution is introduced as the sensor signal is recorded, and then a water rinse is carried out, followed by an air rinse.

It must be pointed out that the operational position and the maintenance position of the sensor are not necessarily different from one another, as is customary with an switching armature, and thus do not have to be located, for example, inside or outside a process container, but it would be possible, at least in principle, for telescoping housing components or similar to be furnished, which seal off the process, while retaining the position of the measuring electrode.

In any case it proves advantageous if only a single pump device is provided, which comprises the several feeds, specifically a first means of supply to provide a cleaning fluid and a second and a third means of supply to provide a first and a second calibration solution, respectively.

Furthermore, it proves to be advantageous if the pump device is a metering pump device, with which specified quantities can be supplied to the rinsing chamber. This proves to be especially advantageous with respect to the calibration solutions which, for cost reasons, should be consumed only in the required quantity.

The pump device could comprise extensive intake ducts equipped with a plurality of selectable valves. However, in a further development of the invention it is proposed that the pump device comprises a first component which can be connected to the several feeds, which has one opening per feed, which openings can be connected selectively to one specific individual intake duct of the pump device.

To achieve this it is further proposed that the device for selectively activating a particular feed has a second component, which is adjustable with respect to the first component, comprising the intake duct, and that the first and the second component are adjustable relative to each other in such a way that one intake port of the intake duct can be selectively connected to a particular feed. Thus the two components are adjusted to each another, specifically rotated, such that a cross-section of the openings on both sides communicate with each other to create a fluid connection between a particular feed and the intake duct of the pump device.

In order to be able to furnish means of supply for the several feeds permanently in place, it proves advantageous if the first component, which is connected to these feeds, is a rigidly mounted component. However, this is not absolutely necessary, since flexible means of supply can also be used for the feeds. Accordingly, it proves to be advantageous if the second component is an actuator moveable with respect to the first rigidly mounted component. The two components under the invention can be rotated with respect to each other, so that it is possible to achieve selective actuation of the particular feeds.

In a further embodiment of the invention the intake duct, which is formed in the second component, is tilted with respect to a rotational axis. Preferably it runs radially inward, but is tilted at the same time. This creates open installation space in the area of the intake port of the intake duct inside the second component, in which control devices, specifically valve control devices, which will be described in detail below, can be housed.

To selectively activate the feeds, the first and the second component specifically and preferably have flange-shaped contact surfaces, lying against one another and specifically rotatable with respect to each other, in which the openings of the first component and the intake ports of the second component open and communicate with one another. In order to rotate the two components relative to each other, a positioning device is provided which is preferably computer controlled.

The positioning device comprises in a preferred embodiment of the invention a positioning means which is moveable linearly, where its adjusting motion runs specifically tangentially to the rotational circle of one component and provides progressive adjustment therefor about one or more rotational positions.

With respect to automation it proves to be advantageous if the device for selectively activating a particular feed comprises furthermore a position control device with which the position of the first and second components can be determined one to the other. In this way the adjusting means can be moved for as long a time until the position control device reports reaching the next following activation position for the particular feed.

In order to realize selective activation of the several feeds it would be conceivable, for example, for the two components to be moveable with respect to each other with adequate sealing. Instead, it has proven to be achievable advantageously, more reliably and involving lower design costs if the openings of the first component can be closed in each instance by valves preloaded in the closing direction, which can then be opened when the appropriate feed is activated.

It is proposed that the valves comprise valve bodies which can be lifted from a valve seat opposite to the feed direction, when the appropriate feed is activated.

Lifting of the valve body could be accomplished per se in any way, for example, electromagnetically. However, it proves to be advantageous if a plunger device is furnished in the second component in the area of the intake opening of the intake duct, which lifts the valve body from its valve seat. The plunger device can, for example and preferably, be furnished in the region above, that is, axially behind the intake port, specifically when the intake duct runs at an angle radially inward—as was already indicated previously. The plunger device is preferably configured in the form of a piston with a push rod, whose free end extends preferably through and beyond the intake port in the direction of the first component. The free end of the push rod can then project into the opening in the first component and lift the valve body from its valve seat. To do this, the plunger piston is preferably preloaded in the opposite direction, so that in its non-activated state its open end does not project beyond the contact surface of the second component. When a feed is to be activated, with the first and second component correctly positioned relative to each other, the plunger piston can be moved against the preload, specifically and preferably pneumatically, so that it opens the valve and creates a communication for flow between the intake duct and the appropriate feed, so that in the following intake stroke by the pump device a preferably predetermined volume of fluid can be drawn in.

In accordance with a preferred embodiment of the invention, the intake duct runs basically radially inward and there opens into a cylindrical chamber, in which an intake and displacement piston can be moved. During the intake stroke, a selected appropriate feed must communicate with the intake port of the intake duct, so that a preferably predetermined volume of transported medium, namely, cleaning fluid or calibration solution or rinsing fluid, is drawn into the cylindrical chamber. In the subsequent displacement stroke, a non-return valve, preferably furnished in the feed, is closed. Moreover, the previously mentioned push rod device, which was furnished as necessary, is activated such that the valve in the opening of the first component closes this opening again. But if the aforementioned non-return valve is additionally furnished, the preload of these valves does not need to be set particularly high.

The intake and displacement piston of the pump device is preferably connected by means of a piston rod means to a moveable control piston in a preferably pneumatic control cylinder. In a preferred embodiment, this control piston is under spring tension in one direction, preferably in the direction of displacement of the intake and displacement piston. This means that only a single pneumatic control connection has to be furnished, with which the piston is moved in the intake direction. The subsequent displacement stroke is carried by spring preloading of the control piston. The pump device can be driven by cycled bursts of compressed air with a piston stroke frequency which can be preset and thus with presettable volumetric displacement. The aforementioned push rod device is driven in exactly the same cycle, which further simplifies the realization of the pump device design.

BRIEF DESCRIPTION OF THE DRAWING

Additional features, details and advantages of the invention are found in the attached patent claims and the drawings and following description of a preferred embodiment of the invention.

In the drawings.

DETAILED DESCRIPTION

Figure 1:
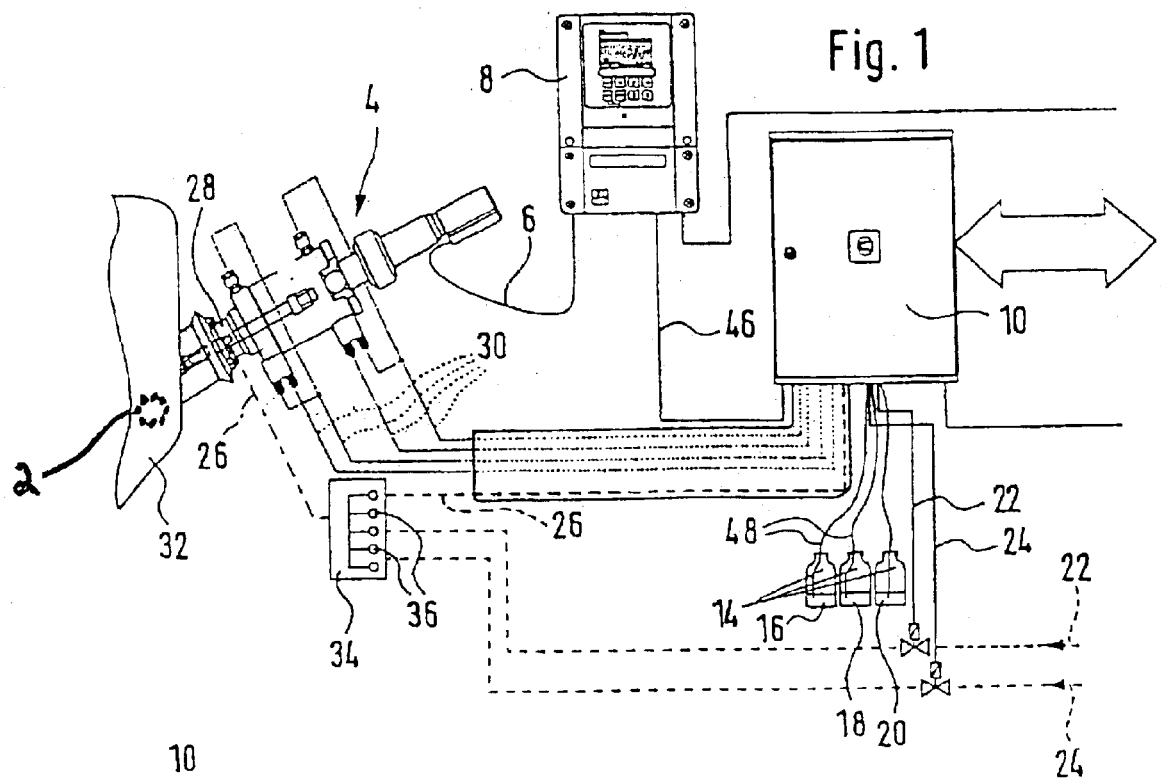
FIG. 1 shows a schematic representation of the inventive measuring, cleaning and calibration device.

FIG. 1 shows a schematic representation of an automatable measuring, cleaning and calibration device for pH-electrodes 2 or electrodes 2 for measuring redox potentials. The electrode 2 is held in an electrode armature 4, called a "switching armature", and connected by a cable 6 to a transducer 8 which is computer-controlled or which comprises a process control computer. A control unit 10 is also shown having a pump unit 12 which can be seen in FIGS. 2 to 5. The pump device 12, which is configured as a metering pump, lifts a cleaning fluid 16, a first and a second calibration solution 18, 20, water under pressure 22 and compressed air 24 from storage containers 14 over a common delivery line 26 into a rinsing chamber 28 for the electrode armature 4 in a manner to be described in greater detail hereafter.

Furthermore, pneumatic control lines 30 lead from the control unit 10 to the electrode armature 4 to move the electrode 2 from, or into, its operating position inside a process container 32, or into or out of a maintenance position shown in FIG. 1. Pneumatically actuated end switches are also provided. Also shown is a rinse block arrangement 34 in the delivery line 26 with a plurality of valves. Through the valves, water under pressure 22 or compressed air 24 can be supplied directly to the electrode armature 4 instead of the medium delivered by the pump device 12. Two additional connections 36 are furnished for additional media, for example, superheated steam, organic cleaner or an additional cleaning agent or cooling air.

Figure 2:
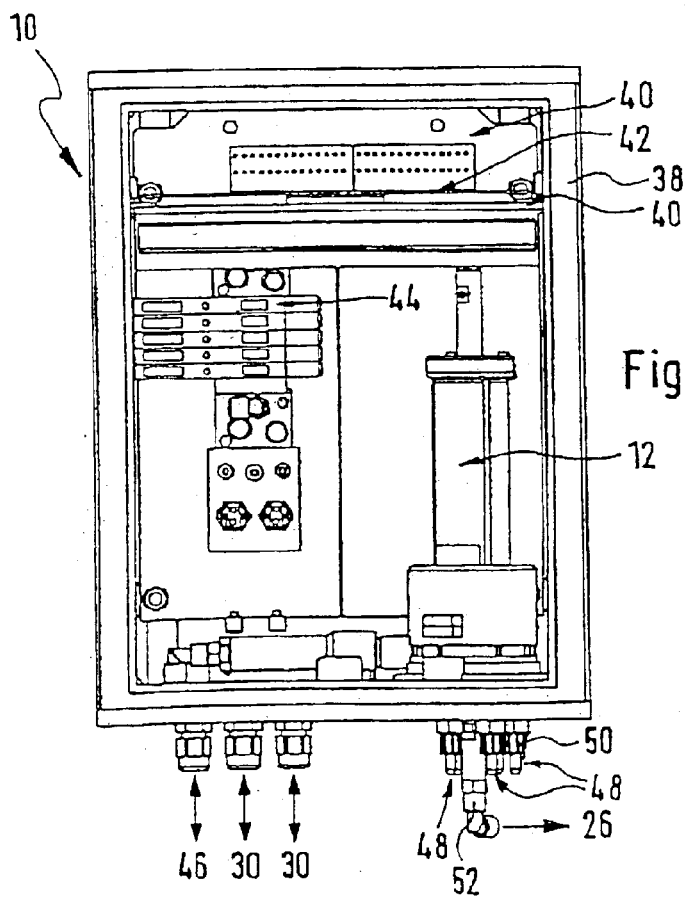
FIG. 2 shows a view of a control unit for the device from FIG. 1 with a pump device.

FIG. 2 shows the inside of the control unit 10, where the single pump device 12 for delivering cleaning fluid 16 and calibration solutions 18 and 20 is housed.

The control unit 10 comprises a housing 38 in which mounting plates are located, such as mounting plates 40, which carry an electronic module 42. Also shown is a piezo-pneumatic valve arrangement 44 for activating the electrode armature 4. The control unit 10 converts commands from the transducer 8, which represents the control center of the measuring arrangement, into pneumatic signals to control the electrode armature 4. Feedback signals about armature position, meaning the position of the electrodes 2, about the fluid level in the canisters 14, and monitoring data for compressed air 24 and water under pressure 22 are processed in the control unit 10. Conversely, measurement signals from the measuring electrode 2, which are sent over the electrode cable 6 to the transducer 8, are also processed there. The transducer 8 is the communications center for the device. The transducer 8 includes a process control computer or is connected to a process control computer and an input device. It controls signal paths and is linked over an RS 485 bidirectional interface 46 to the control unit 10 where the signals and control commands from the process control computer are converted into pneumatic magnitudes to control the pump device 12 and to activate the electrode armature 4, or these signals and commands are carried out. As already mentioned, feedback, such as armature position, canister fluid level and monitoring of compressed air and water is sent over this interface to the process control computer.

As already indicated, feed lines 48 lead from the supply containers 14 to the single pump device 12. Additional feed lines 48 carry water under pressure 22 and compressed air 24. The connection of the feed lines 48 to the pump device 12 cannot be seen from FIG. 1. FIG. 2, however, shows three of a total of five connectors 50 positioned concentrically in a circle for the feed lines 48. This means that all the feed lines 48 discharge into this single pump device 12, which will described in more detail below. The pump device 12 is configured such that the five connections 50 can be activated selectively, so that the pump device 12 can selectively lift the particular media—cleaning fluid, calibration solutions, compressed air, water—through the five feed lines 48 and through the common delivery line 26 to the electrode armature 4. A pump output 52 leads inside the concentrically arranged connections 50 in FIG. 2 down and away and forms an angled connection for the delivery line 26.

Figure 3:
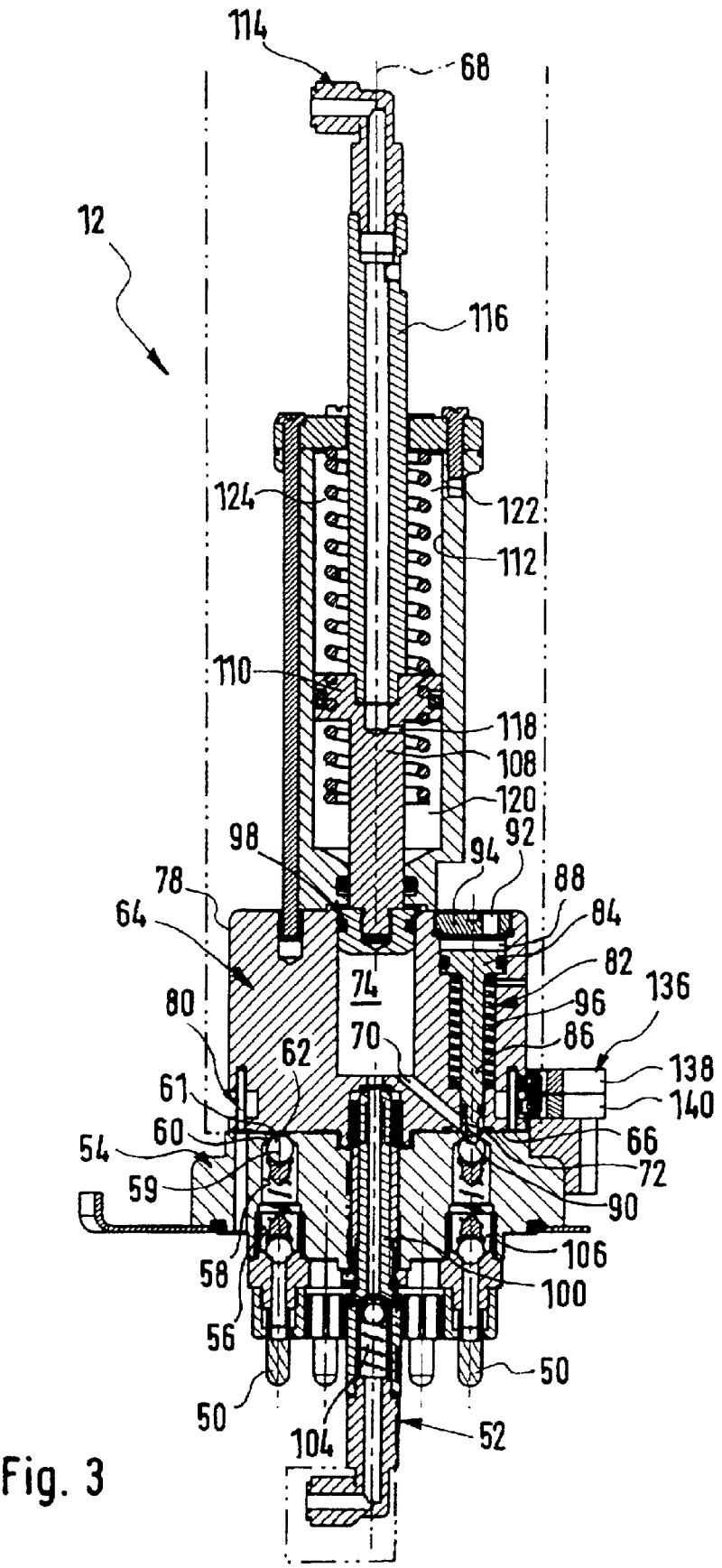
FIG. 3 shows a longitudinal section of the pump device depicted in FIG. 2.
Figure 4:
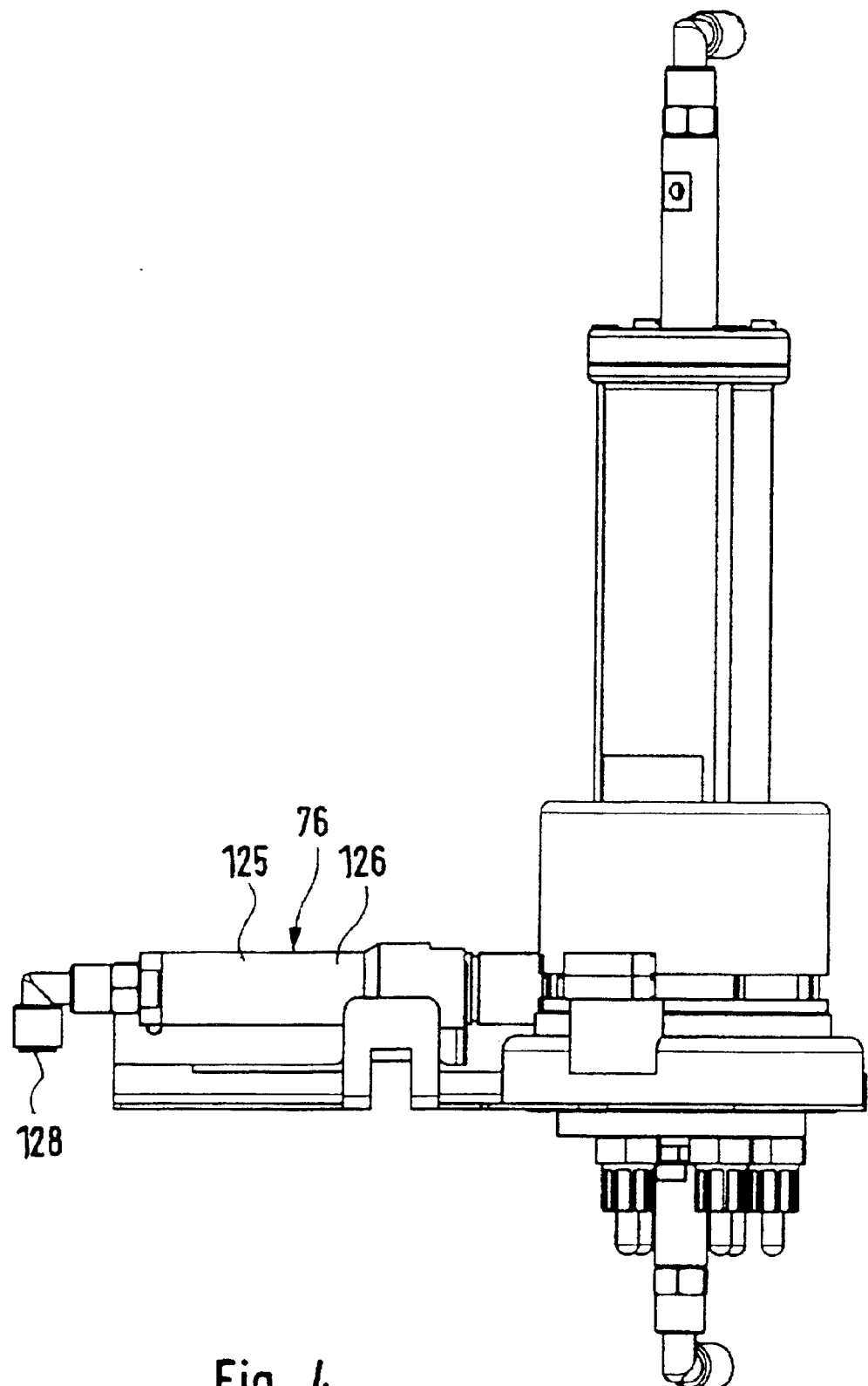
FIG. 4 shows a side view of the pump device from FIG. 1.
Figure 5:
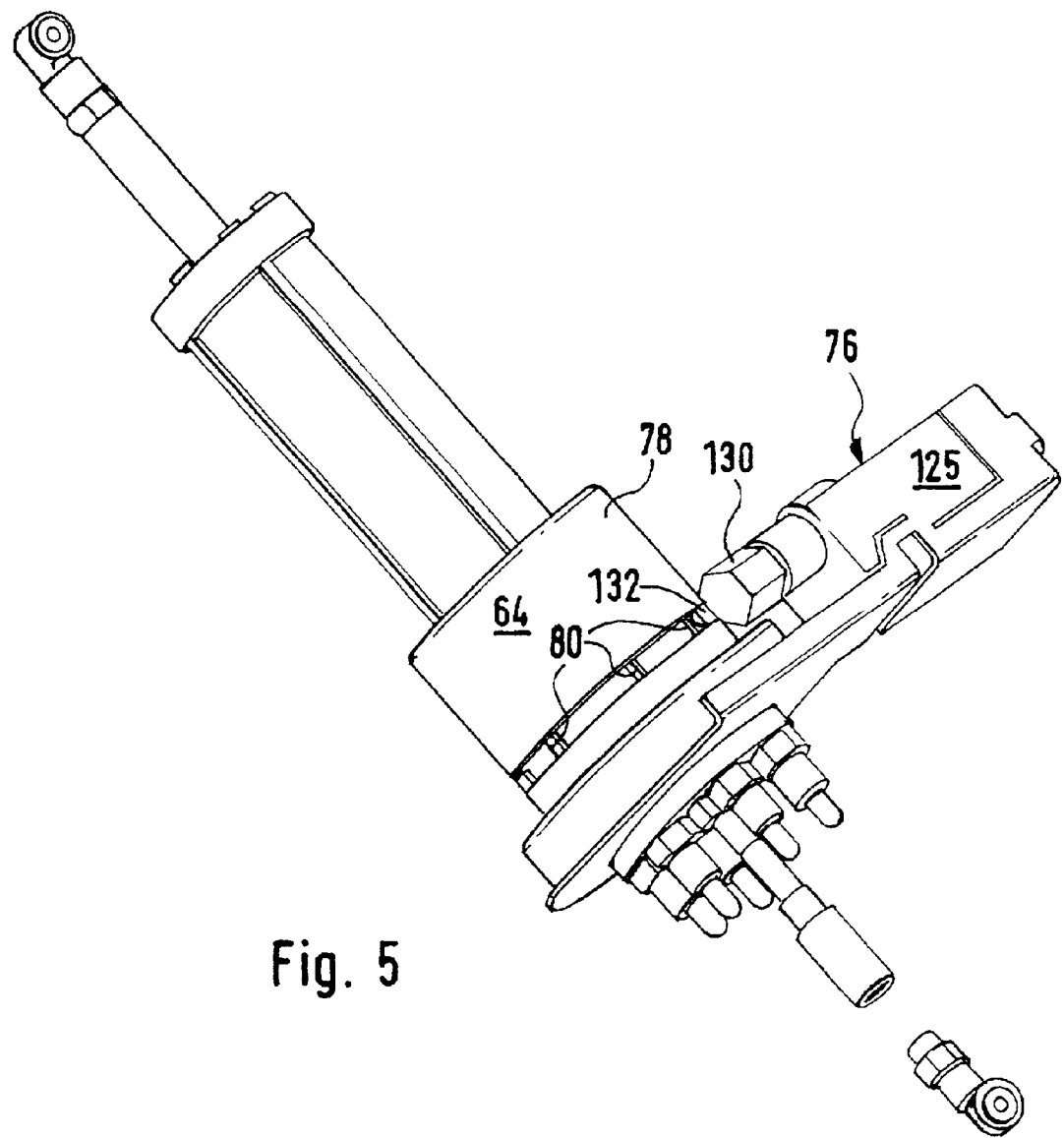
FIG. 5 shows an isometric view of the pump device from FIGS. 3 and 4.

Construction and operation of the single pump device 12 are explained below with the aid of FIGS. 3 and 4. FIGS. 3 and 4 show a sectional view and a side view of the single inventive pump device 12. The pump device 12 comprises a first rigidly attached component 54, into which the connections 50 are threaded into axial bores 56 as male parts. The specific axial bores 56 form transverse ports 58 running in an axial direction through the first component 54. However, the transverse ports 58 narrow through the first component 54 and form a conical valve seat 60 for a valve body 59. All five transverse ports 58 open into the connection to the particular valve seat 60 in the form of orifices 61 in a flange-shaped connecting surface 62 in the first component 54. The pump device 12 includes a second rotatable component 64 opposite the first component 54. This second component 64 lies against the contact surface 62 with a contact surface 66 complementary to the contact surface 62.

In the second component 64, which can be rotated about a longitudinal center axis 68 of the pump device 12, an intake duct 70 is formed, which, starting from an intake port 72 in the contact surface 66, runs radially inward but is inclined at an angle to the longitudinal center axis 68 and angled upward and opens into a central cylindrical chamber 74.

By rotating the second component 64 with respect to the first component 54, one of the connections 50 and thus one of the feed lines 48 can be selectively activated, by performing the rotation such that the intake port 72 of the intake duct 70 coincides with the orifices 61 of the transverse ports 58 in the contact surface 62, so that a fluid communication path exists. The rotation of the second component 64 with respect to the first component 54 is carried out by a device 76, which will be described in more detail below and which engages steps or pins 80 furnished on the circumference 78 of the second component 64 and thus rotates the second component 64.

In order to achieve a fluid communication between the transition ports 58 in the first component and the intake duct 70 in the second component 64, the valve body 59 has to be lifted from the conical valve seat 60, in other words against the direction of feed. This is done by a push rod device 82, which comprises a pneumatically actuatable piston 84 and a push rod 86. The piston 84 with the push rod 86 is housed in an offset axial bore 88 in the second rotatable component 64, such that the free end 90 of the push rod 86 protrudes beyond the contact surface 66 through the intake port 72. The free end can then extend into the opening 61 of the transition port 58 and lift the valve body 59 from its valve seat 60, so that a fluid communication with the intake duct 70 is created. It should be mentioned that the piston 84 with the push rod 86 is driven by pneumatic control pressure which is supplied through a connecting opening 92 in a cover 94, which cover 94 closes the axial bore 88 in a pressure-tight manner. When pneumatic pressure is removed, the piston 84 and the push rod 86 are returned by a spring 96, so that the valve body 59 is pushed against the valve body 60 again by spring preload in a sealing fashion.

When, while a fluid communication exists, an intake and displacement piston 98 is moved upward, that is, into the position shown in FIG. 3, the particular fluid medium is drawn out of the feed line 48 into the cylindrical chamber 74 through the intake port 70, the transverse port 58 and the connections 50. In the ensuing displacement stroke of the piston 98, basically the entire volume of the cylindrical chamber 74 filled with fluid is moved, or displaced, through a central axial outlet pipe 100 to the pump outlet 52. In the outlet pipe 100, a valve 104 is preloaded against the direction of flow, the closing effort of which is calculated such that the valve 104 opens under the displacement pressure of the piston 98. The delivery line 26 is attached to the open end of the angled pump outlet 52.

It should be mentioned that during the displacement stroke of piston 98, the specific non-return valve 106 furnished in the connection 50 closes anyway, but it still proves advantageous if the valve body 59 is also again seated against its valve seat 60 in a sealing fashion by moving the push rod 86 back. After completion of the displacement stroke a further feed line 48, or a further connector 50 respectively, can be activated without fluid medium present in the transition ports 58 escaping into the area between the contact surfaces 62 and 66.

The intake and displacement piston 98 is connected through a piston rod 108 running in an axial direction to a second control piston 110, which can be moved in a control cylinder 112. The control cylinder 112 is located in an axial direction on the side of the second component 64 opposite the first component 54. The control cylinder 112 is activated by a pneumatic connection 114 axially opposite the pump outlet 52. The pneumatic connection 114 provides compressed air over a tube 116 screwed to the control piston 110 through the control piston 110 and over a transverse bore 118 in a part 120 of the control piston 110 facing the first component 64, so that when pressure is applied, the control piston 110 and with it the piston rod 108 and the intake and displacement piston 98 is moved upward, in the intake direction. A return spring 124 is located in the other part 122 of the control cylinder 112, which is supported against one side of the control piston 110 and moves the latter downward when pressure is removed, in the displacement direction, whereby the displacement stroke of the piston 98 is carried out.

It should be mentioned that compressed air is applied to the push rod device 82 in the same cycle as to the pneumatic connection 114, and thus the control piston 10. The result of this is that the appropriate valve body 59 is always lifted from its valve seat 60 at the moment of the intake stroke of the piston 98, so that a fluid communication is present. On the ensuing displacement stroke, on the other hand, the free end of the push rod 86 is pulled back again below the contact surface 66, so that the valve body 59 again lies in a sealing fashion against its valve seat 60.

The aforementioned device 76 for rotating the second component 64 with respect to the first rigidly attached component 54 shall now be explained. As can be seen from FIG. 4, the device 76 comprises a pneumatic positioning device 125 having a pneumatic cylinder 126 with a compressed air connection 128 and a linearly moveable positioning means 130 inside the cylinder 126. As can be seen from the isometric view in FIG. 5, the direction of adjustment of the positioning means 130 is aligned tangentially to the direction of rotation and to the circumference 78 of the second component 64. The positioning means 130 has a rack-like carrier 132 on the side facing the circumference of the rotatable component 64, which engages the previously mentioned steps or pins 80 on the circumference 78 of the component 64 and, as result of the motion of the positioning means 130, rotates the component 64 around its longitudinal center axis 68.

Furthermore, a position control device 136 is provided (FIG. 3), which comprises two microswitches 138, 140 positioned one above the other for position feedback and for the zero position.

When a maintenance process is performed according to set programs, a corresponding command is given by the process control computer in the transducer 8 to the control unit 10, and from there the measuring electrode 2 is moved from its operational position into the maintenance position shown in FIG. 1 by means of the pneumatic control lines 30. A maintenance program, as was mentioned at the beginning, can then be carried out by selectively activating the feed lines 48. To do this, the component 64 is rotated with respect to component 54 by means of the pneumatic positioning device 125 such that a suitable connection 50, and thus over the appropriate feed line 48, a specific container 14 is selected. It is also possible that a rinse with water under pressure 22 is carried out and only then is the container 14 with the cleaning fluid 16 selected and fed to the rinsing chamber 28 for the electrode armature 4 over the single pump device 12 and the delivery line 26.

Cleaning or calibration programs can be freely adapted to the specific requirements by means of the process control computer. Cleaning and calibration media can be selected, if necessary, additional media can be supplied over the rinsing block arrangement 9, and the number and sequence of the steps can be varied as desired.

Program-controlled maintenance procedures can be carried out, for example, according to specifiable time intervals. It is also possible that a sensor test device in the transducer is operated, which gives a signal to perform a maintenance procedure in the event that the sensor deviates too quickly, and that such a maintenance program is subsequently performed. It is furthermore conceivable that following each mains power outage, a maintenance procedure is automatically performed.

What is claimed is:

1. An automatable measuring, cleaning and calibrating device for pH-electrodes or electrodes for measuring redox potentials, having an electrode armature which keeps the measuring electrode in one of an operating position and in a maintenance position, where the electrode is retained in the maintenance position in a rinsing chamber in which a cleaning and calibration process can be carried out, and having a pump device for supplying cleaning fluid and calibration solution to the rinsing chamber over a delivery line connecting the pump device and the rinsing chamber, characterized in that the pump device comprises several feeds on its intake side, an another device is provided for selectively activating a specific feed and a media selectively brought over the several feeds to the pump device reaches said rinsing chamber over a common delivery line, the pump device including a first component connectable with the several feeds which has one opening per feed, the openings being selectively connectable to an intake duct on the pump device, the another device for selectively activating one feed having a second component adjustable with respect to the first component, the second component including the intake duct, and the first and second components being adjustable with respect to each other such that an intake port in the intake duct is selectively connectable to a specific feed.

2. The device in accordance with claim 1, wherein the electrode armature is a switching armature which moves the measuring electrode between the operating position and the maintenance position.

3. The device in accordance with claim 1, wherein the several feeds comprise a first means of supply for providing a cleaning fluid and a second means and a third means of supply for providing a first and second calibration solution, respectively.

4. The device in accordance with claim 1, wherein the pump device is a metering pump device with which specified quantities can be supplied to the rinsing chamber.

5. The device in accordance with claim 1, wherein the first component is a stationary component.

6. The device in accordance with claim 1, wherein the second component is a moveable actuator.

7. The device in accordance with claim 1, wherein the first and the second component are rotatable with respect to one another.

8. The device in accordance with claim 1, wherein the intake duct is inclined with respect to an axis of rotation.

9. The device in accordance with claim 1, wherein the openings in the first component are located concentrically to the axis of rotation.

10. The device in accordance with claim 1, wherein the first and a second component have flange-like contact surfaces contacting each other and specifically rotatable with respect to each other, in which the openings of the first component and the intake duct of the second component open.

11. The device in accordance with claim 1, wherein rotation of the components with respect to each other is achievable by means of a positioning device.

12. The device in accordance with claim 11, wherein the positioning device comprises a linearly moveable means of adjustment, whose positioning motion runs tangentially to the rotation of the first component and progressively adjusts it by one or more rotational settings.

13. The device in accordance with claim 1, wherein the another device for selectively activating one feed comprises a position control apparatus with which the position of the first and of the second component to each other can be determined.

14. The device in accordance with claim 1, wherein the openings of the first component are closable by valves preloaded in the closing direction, which are openable when the particular feed is activated.

15. The device in accordance with claim 14, wherein the valves comprise valve seats which are liftable from a valve seat counter to the feed direction when the particular feed is activated.

16. The device in accordance with claim 15, wherein a push rod device is furnished in the second component in the area of the intake port of the intake duct, which lifts the valve body from its valve seat.

17. The device in accordance with claim 1, wherein the intake duct runs radially inward and there opens into a cylindrical chamber in which an intake and displacement piston is moveable.

18. The device in accordance with claim 1, wherein an intake and displacement piston is connected in a driving manner by means of a piston rod device to a control piston moveable in a pneumatic control cylinder.

19. The device in accordance with claim 18, wherein the control piston is spring-loaded in the displacement direction of the intake and displacement piston.

* * * * *